(12) United States Patent
Dos Santos

(10) Patent No.: US 9,132,034 B2
(45) Date of Patent: Sep. 15, 2015

(54) VALVE POSITION SENSOR

(71) Applicant: Alcon Research, Ltd., Fort Worth, TX (US)

(72) Inventor: Cesario P. Dos Santos, Aliso Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 243 days.

(21) Appl. No.: 13/632,550

(22) Filed: Oct. 1, 2012

(65) Prior Publication Data
US 2014/0094736 A1  Apr. 3, 2014

(51) Int. Cl.
*A61F 9/007* (2006.01)
*A61M 39/22* (2006.01)

(52) U.S. Cl.
CPC .......... *A61F 9/00781* (2013.01); *A61M 39/227* (2013.01)

(58) Field of Classification Search
CPC .......................... A61M 39/227; A61F 9/00781
USPC ....................................................... 604/9, 31
See application file for complete search history.

(56) References Cited

U.S. PATENT DOCUMENTS

| | | | | |
|---|---|---|---|---|
| 3,932,722 A | * | 1/1976 | Obata et al. | 200/513 |
| 6,048,328 A | * | 4/2000 | Haller et al. | 604/288.03 |
| 6,692,457 B2 | * | 2/2004 | Flaherty | 604/67 |
| 2009/0275924 A1 | | 11/2009 | Lattanzio et al. | |
| 2009/0306585 A1 | | 12/2009 | Pang et al. | |
| 2013/0085440 A1 | * | 4/2013 | Bohm et al. | 604/9 |
| 2013/0150775 A1 | | 6/2013 | Dos Santos et al. | |
| 2013/0150776 A1 | | 6/2013 | Bohm et al. | |
| 2013/0211313 A1 | | 8/2013 | Dos Santos et al. | |

OTHER PUBLICATIONS

Partial European Search Report and Annex to the European Search Report issued for European Application EP13189921 dated May 21, 2014, 6 pages.

* cited by examiner

*Primary Examiner* — Leslie Deak
*Assistant Examiner* — Kai Weng
(74) *Attorney, Agent, or Firm* — Haynes & Boone, LLP

(57) ABSTRACT

An IOP control device for implantation in an eye of a patient is disclosed, including a housing with an entrance port and an exit port, a membrane anchored within the housing in a manner forming a flow control chamber on a first side of the membrane and a fluid flow passageway on a second opposing side of the membrane, and a position sensor system. The flow control chamber is arranged to contain a gas creating a flow control chamber pressure, and the membrane is configured to affect flow through the fluid flow passageway from the entrance port to the exit port by deflecting in response to changes in the flow control chamber pressure. The position sensor system includes a first conductive portion and a second conductive portion positioned to selectively contact the first conductive portion to indicate the position of the membrane relative to the fluid flow passageway.

39 Claims, 4 Drawing Sheets

VALVE POSITION SENSOR

BACKGROUND

The present disclosure relates generally to valves and associated systems and methods. In some instances, embodiments of the present disclosure are configured to be part of an IOP control system for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 170. The angle of the anterior chamber 170, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the anterior chamber of the eye to a drainage site, relieving pressure in the eye and thus lowering IOP. In order to provide consistency and accuracy in fluid flow through the drainage device, it may be important to monitor the open and closed condition of the drainage device to maximize the efficiency of the device and to limit changes and degradation that may occur in the drainage device over time.

The system and methods disclosed herein overcome one or more of the deficiencies of the prior art.

SUMMARY

In one exemplary aspect, this disclosure is directed to an IOP control device for implantation in an eye of a patient, comprising a housing, a membrane, and a position sensor system configured to detect the position of the membrane. The housing is sized for implantation into the eye of the patient and includes an entrance port and an exit port. The membrane is anchored within the housing in a manner to form a flow control chamber on a first side of the membrane and a fluid flow passageway on a second opposing side of the membrane. The flow control chamber includes a flow control chamber pressure and the fluid flow channel includes a fluid flow channel pressure. The membrane is configured to affect flow through the fluid flow passageway from the entrance port to the exit port by deflecting in response to pressure differentials of the flow control chamber pressure and the fluid flow channel pressure acting on the opposing sides of the membrane. The position sensor system includes a first conductive portion and a second conductive portion positioned to selectively contact the first conductive portion to indicate the position of the membrane relative to the fluid flow passageway.

In one exemplary aspect, the present disclosure is directed to an IOP control system for implantation in an eye of a patient, comprising a drainage tube configured to convey aqueous humor from an anterior chamber of the eye and a flow system in fluid communication with the drainage tube. The flow system includes a housing, a membrane, and a position sensor system. The housing includes a valve seat positioned between an entrance port and an exit port from the drainage tube. The membrane is anchored within the housing to form a flow control chamber having a flow control chamber pressure on a first side of the membrane. The implantable device is actuatable in response to a flow control chamber pressure and the membrane is configured to control flow rates of the aqueous humor along the drainage tube by deflecting in response to the flow control chamber pressure. The position sensor system includes a first conductive portion positioned on the membrane and a second conductive portion positioned on the valve seat between the entrance port and the exit port.

In another exemplary embodiment, the present disclosure is directed to a method of regulating drainage from an anterior chamber of an eye with an implantable device. The method comprises directing fluid from an entrance port through a fluid flow passageway formed in part by a flexible membrane, the membrane configured to deflect away from and toward a valve seat to throttle flow by increasing or decreasing the size of the fluid flow passageway; determining a valve state of the implantable device using a position sensor system configured to detect a position of the membrane relative to the valve seat; and modifying the amount of drainage through the implantable device in response to a flow control pressure acting on the membrane by deflecting the membrane to increase or decrease the size of the fluid flow passageway based on the valve state of the implantable device.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
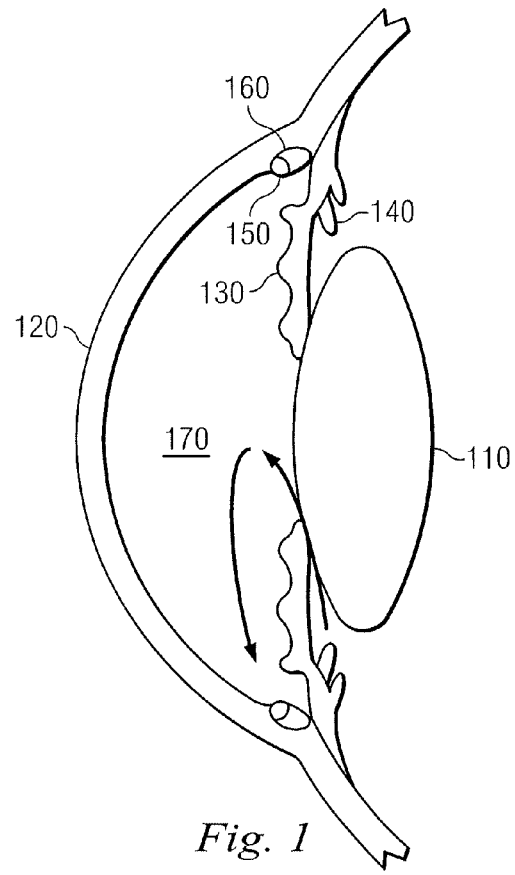
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to a position sensor system usable in the operation of membrane valves. In some instances, embodiments of the present disclosure are configured to be used in the operation of electrolysis-based membrane valves. In some instances, embodiments of the present disclosure are configured to be part of an TOP control system. Those of skill in the art will realize that the position sensor systems disclosed herein may be utilized in alternative applications requiring membrane deflection to selectively open and close a valve.

The position sensor systems disclosed herein are comprised of conductive elements on the membrane and the valve housing that are shaped and configured to electrically interact to indicate the position of the membrane relative to the valve housing, thereby informing the control system whether the valve is in an open or closed condition. Thus, by informing the control system whether the valve is in an open or closed condition, the position sensor systems disclosed herein may provide a closed loop feedback method allowing the control system to use power only when necessary in embodiments involving electrolysis-based membrane valves. Moreover, the incorporation of a position sensor system may allow for minimization of power consumption and extension of battery life, thereby increasing the longevity of valve actuation and potentially the life of the product, such as an implant. In embodiments involving electrolysis-based membrane valves, the position sensor systems disclosed herein provide the safety feature of preventing the control system from inappropriately over-pressurizing the membrane in situations when the valve is already in a desirable condition (i.e., open or closed for a given pressure state), thus preventing inadvertent damage to the membrane. Thus, the position sensor systems disclosed herein may improve or optimize the performance of IOP control systems utilizing membrane valves.

Figure 2:
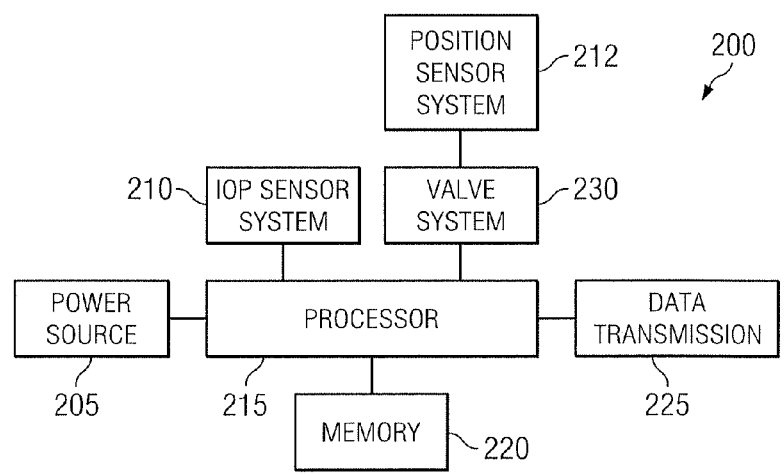
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a position sensor system 212, a processor 215, a memory 220, a data transmission module 225, and a flow system described as a valve system 230.

The power source 205, which provides power to the system 200, is typically a rechargeable battery, such as a lithium ion or lithium polymer battery, although other types of batteries may be employed. The power source can be recharged via inductive coupling such as an RFID link or other type of magnetic coupling.

The IOP sensor system 210 is described below with reference to FIG. 3, and the position sensor system 212 and the valve system 230 are described below with reference to FIGS. 4 and 5.

The processor 215 is typically an integrated circuit with power, input, and output pins capable of performing logic functions or choices. For example, the processor 215 may perform logic functions based on inputs from the IOP sensor system 210 and/or the position sensor system 212 to determine the operating status of the IOP control system 200, including the open or closed condition of the valve system 230. In some embodiments, the processor 215 controls the supply of power from the power source 205 to the valve system 230. In various embodiments, the processor 215 may be a targeted device controller or a microprocessor configured to control more than one component of the device.

The memory 220, which is typically a semiconductor memory such as RAM, FRAM, or flash memory, interfaces with the processor 215. As such, the processor 215 can write to and read from the memory 220, and perform other common functions associated with managing semiconductor memory. In this manner, a series of IOP readings can be stored in the memory 220.

The data transmission module 225 may employ any of a number of different types of data transmission. For example, in various embodiments, the data transmission module 225 may be an active device such as a radio or a passive device with an antenna on an RFID tag. Alternatively, the data transmission module 225 may be activated to communicate an elevated IOP condition to a secondary device such as a PDA, cell phone, computer, wrist watch, custom device exclusively for this purpose, remote accessible data storage site (e.g. an interne server, email server, text message server), or other electronic device or service.

Figure 3:
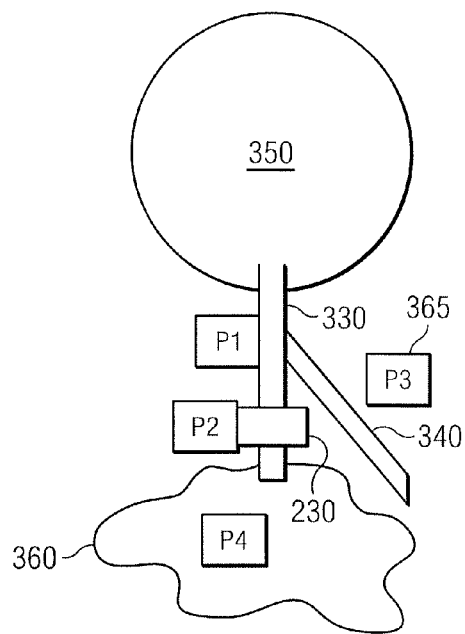
FIG. 3 is a schematic diagram of an exemplary IOP control system according to the principles of the present disclosure disposed within an eye.

FIG. 3 is a diagram of the exemplary IOP sensor system 210 disposed about a representation of an eye, a drainage tube 330, the valve system 230, and a divider 340. In FIG. 3, the exemplary IOP sensor system 210 (shown in FIG. 2) includes four pressure sensors, P1, P2, P3, and P4. The pressure sensor P1 is located in or is in fluidic communication with an anterior chamber 350, the pressure sensor P2 is located to measure intermediate pressures found within the valve system 230, the pressure sensor P3 is located remotely from P1 and P2 in manner to measure atmospheric pressure, and the pressure sensor P4 is located at a drainage site 360 in the subconjunctival space and is arranged to measure drainage pressure, such as a bleb pressure. In some embodiments, the IOP sensor system includes three pressure sensors, corresponding to the sensors P1, P3, and P4 shown in FIG. 3. In particular, in IOP control systems including a non-electrolysis, pressure differential membrane valve system, the IOP control systems may lack a pressure sensor located to measure intermediate pressures within the valve system (e.g., the pressure sensor P2).

In some embodiments, the pressure sensor P1 is located in a lumen or tube that is in fluid communication with the anterior chamber, such as the drainage tube 330. The pressure sensor P4 may be located in a pocket at the drainage site 360, such as a bleb, that generally contains aqueous humor or in communication with such a pocket, via a tube for example, and is in the wet site 360. The drainage site 360 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye.

The drainage tube 330 drains aqueous humor from the anterior chamber 350 of the eye. The valve system 230 controls the flow of aqueous humor through the tube 330. In the embodiment shown, the pressure sensor P1 measures the pressure in the tube 330 upstream from the valve system 230 and downstream from the anterior chamber 350. In this manner, pressure sensor P1 measures the pressure in the anterior chamber 350. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the system includes barriers that separate the sensors P1, P2, P3, and P4. These barriers may be elements of the system itself. For example, in FIG. 3, the pressure sensor P3 is physically separated from the pressure sensor P4 by the divider 340. The divider 340 is a physical structure that separates the wet site 360 of P4 from the dry site 365 of P3. In one example, the barrier separating the anterior chamber pressure sensor P1 and the drainage site pressure sensor P4 is the valve system 230.

Generally, IOP is a gauge pressure reading—the difference between the absolute pressure in the eye (as measured by P1) and atmospheric pressure (as measured by P3). In one embodiment of the present disclosure, pressure readings are taken by the pressure sensors P1 and P3 simultaneously or nearly simultaneously over time so that the actual IOP can be calculated (as P1−P3 or P1−f(P3), where f(P3) indicates a function of P3). The pressure readings of P1 and P3 can be stored in memory 220 by the processor 215. They can later be read from memory so that actual IOP over time can be interpreted by a physician.

The pressure sensors P1, P2, P3, and P4 can be any type of pressure sensors suitable for implantation in the eye. They each may be the same type of pressure sensor, or they may be different types of pressure sensors.

Since the pressure sensor P1 measures the pressure in the anterior chamber 350 and pressure sensor P4 measures pressure at the drainage site 360, the difference between the readings taken by these two pressure sensors (P1-P4) provides an indication of the pressure differential between the anterior chamber 350 and the drainage site 360.

In one embodiment, this pressure differential dictates the rate of aqueous humor flow from the anterior chamber 350 to the drainage site 360.

Readings from the pressure sensors P1, P2, P3, and P4 can be used to control the flow rate through the tube 330 by controlling the valve system 230. For example, the valve system 230 may be controlled based on the pressure readings from pressure sensors P1, P2, P3, and P4. The valve system 230 may be controlled by the processor 215 based on input data received from the sensors. A desired pressure differential (that corresponds to a desired flow rate) can be maintained by controlling the operation of the valve system 230. Likewise, various intraocular pressure parameters, such as, by way of non-limiting example, the desired IOP, the TOP change rate, and/or the bleb pressure may be controlled by controlling the operation of valve system 230. Note that in some exemplary embodiments, the physician may be able to set the high/low IOP thresholds wirelessly to meet each patient's specific requirements.

The valve system 230 is disposed along, and may form a part of, the drainage tube 330 between the tube end in the anterior chamber 350 and the drainage site 360, as shown in FIG. 3. The valve system 230 is configured to control the flow of drainage fluid through the drainage tube 330, and thereby control pressure in the eye, including the IOP. For example, when IOP is high, the valve system 230 may operate to permit increased flow through the drainage tube, and when IOP is low, the valve system 230 may operate to decrease the flow through the drainage tube. In addition, some embodiments of the valve system 230 are configured to monitor and control the flow of drainage fluid to the drainage site 360 or bleb, and thereby control the bleb pressure to maintain a desired fluid flow to the bleb. This may decrease fibrosis and increase absorption efficiency. To accomplish this, the valve system 230 is responsive to signals sent as instructions from the processor 215, shown in FIG. 2. The processor 215 is responsive to information received from the position sensor system 212 and the pressure measurements taken by the pressure sensors P1, P2, P3, and P4, and/or the IOP, as explained above. Although described as a valve system, the flow system may be one or more valves, one or more pumps, or a combination of valves and pumps, or other flow devices for regulating or otherwise affecting flow.

Figure 4:
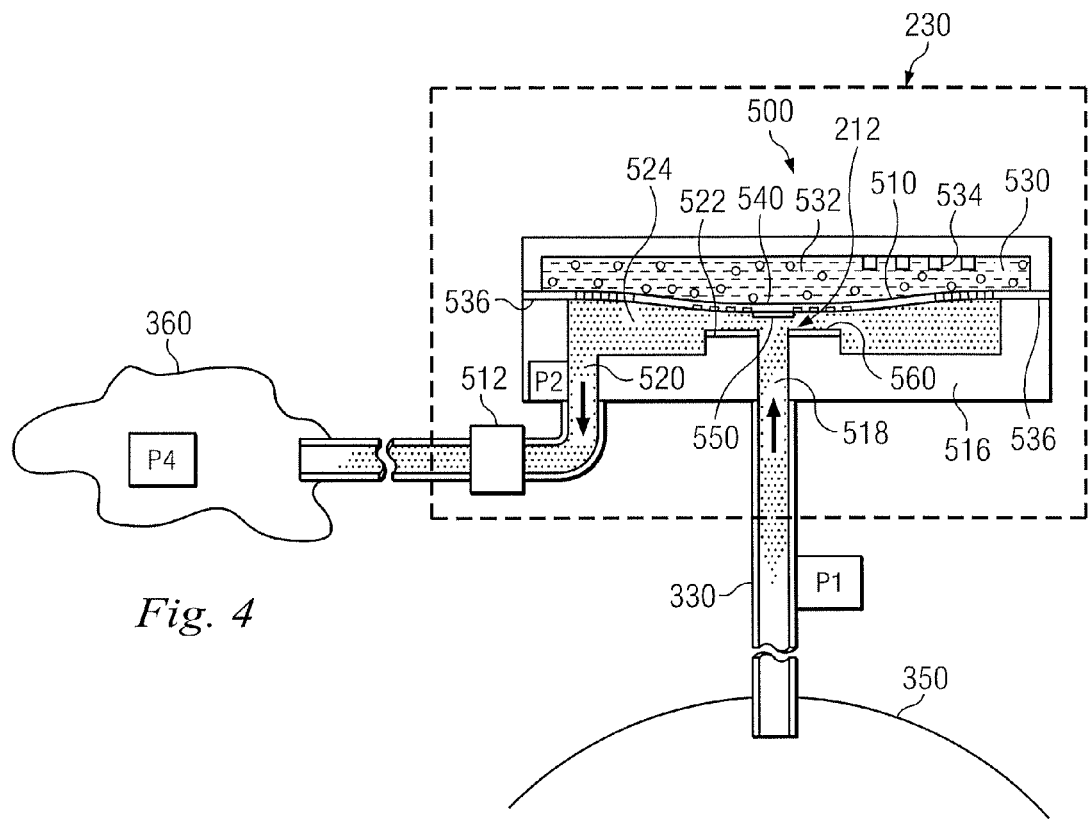
FIG. 4 is an illustration of a cross-sectional view of a portion of an exemplary IOP control system in an open condition according to one embodiment consistent with the principles of the present disclosure.

FIG. 4 shows an exemplary embodiment of an electrolysis-based membrane valve 500 that may form a part of the valve system 230. The membrane valve 500 includes an exemplary embodiment of the position sensor system 212, which is shown in greater detail in FIG. 5.

In the embodiment shown in FIG. 4, the membrane valve 500 includes a membrane 510 anchored within a housing 516. The housing 516 includes an entrance port 518 and an exit port 520, a valve seat 522 in the housing 516, and a fluid flow passageway 524 extending between the entrance port 518 and the exit port 520. The valve 500 is configured to selectively allow or block aqueous humor flowing from the anterior chamber 350 through the drainage tube 330 to any subsequent flow control structures 512 within the valve system 230 or to the drainage site 360. The housing 516 is configured to connect with the drainage tube 330 such that deflection of the membrane 510 at least partially opens and closes the valve 500 to the outflow of aqueous humor. The entrance port 518 connects to the drainage tube 330 and is configured to receive aqueous humor flowing from the drainage tube 330 into the valve system 230. The exit port 520 permits fluid to exit the housing 516 for further regulation within the other structures 512 or for release at the drainage site 360. In other embodiments, the housing of the membrane valve may include any of a number of entrance ports and exit ports arranged in a variety of configurations.

The membrane valve 500 also includes a flow control chamber 530, actuator fluid 532 in the flow control chamber 530, and electrodes 534 arranged to cooperate with the actuator fluid 532. The chamber 530 is sealed closed and separated from the fluid flow passageway 524 by the membrane 510. Accordingly, as pressure increases within the chamber 530, the membrane 510 displaces in the direction of the fluid flow passageway 524.

The actuator fluid 532 is contained in the flow control chamber 530 and includes, in some embodiments, water. Some embodiments include a saline such as sodium chloride in solution or other salts. Other embodiments include other forms of electrolytes such as sulfuric acid, sodium bicarbonate, potassium nitrate, lithium sulfate, copper sulfate, magnesium sulfate and others.

The electrodes 534 are disposed within the actuator fluid 532 in a manner permitting at least a portion of the ions and electrolytes in the actuator fluid 532 to phase change from liquid to gas, forming gas-filled bubbles through electrolysis. As the bubbles form, the pressure in the chamber 530 increases, thereby increasing the overall pressure. This increased pressure acts on the membrane 510 to cause its displacement. The electrodes 534 are in electrical communication with the power source 205, which is controlled by the processor 215. Through the electrolysis, water in the actuator fluid 532 may result in hydrogen and oxygen molecules.

The membrane 510 comprises a flexible, deformable, fluid-tight membrane or diaphragm anchored to the housing 516. The membrane 510 provides valve functionality by deflecting in response to pressure differentials across its opposing sides. In the pictured embodiment, the membrane 510 is anchored within the housing 516 at a peripheral zone 536 of the membrane 510. As described further below in reference to FIG. 6, the membrane 510 includes corrugation features (such as ridges and valleys) whose depths affect the deflection profile of the membrane in response to various pressures. In some embodiments, the membrane is substantially flat, without corrugation features. The membrane 510 includes two generally parallel surfaces, a surface 510a and an opposite surface 510b. The surface 510a faces the interior of the flow control chamber 530 (i.e., in contact with the actuator fluid 532), and the surface 510b is adjacent the fluid flow passageway 524 (i.e., in contact with the fluid passing through the valve 500).

The membrane 510 deflects in response to pressure differentials across the membrane to open and close the valve. When the membrane 510 is deflected away from the valve seat 522, fluid flows from the drainage tube 330 into and through the membrane valve 500 and any other structures 512, such as, by way of non-limiting example, valves, pumps, and/or check valves, and then exits the valve system 230 to enter the drainage site 360.

The membrane 510 can be formed of any suitable biocompatible material that can move, flex, deform, or deflect in response to pressure. In some embodiments, the membrane 510 is constructed of a micro-electromechanical system (MEMS) membrane, such as, but not by way of limitation, a Parylene membrane. The membrane 510 may have a thickness ranging from 1 to 15 μm.

The valve seat 522 concentrically overlies the entrance port 518 and a central aperture of the valve seat 522 serves as the entrance to the fluid flow passageway 524. In the pictured embodiment, the valve seat 522 is shaped and configured as a raised, generally annular or toroid component. In other embodiments, the valve seat 522 is an inner floor surface of the housing 516. The valve seat 522 is positioned between the entrance port 518 and the exit port 520 such that fluid flows from the entrance port 518, through the fluid flow channel 524, and out the exit port 520.

In the pictured embodiment, the components of the valve 500 are generally circular in geometry. Accordingly, the membrane 510 may be shaped and configured as a generally circular structure that is secured at the peripheral zone 536 to the housing 516 and symmetric about the valve seat 522. As such, as the volume or pressure increases within the chamber 530, a central portion 540 of the membrane 510 provides the greatest level of displacement or deflection toward the valve seat 522. In other embodiments, the housing and membrane may be formed so that the membrane and the valve seat have a non-circular shape, including oval, substantially rectangular, or square, for example. Other shapes are also contemplated.

In the example shown in FIG. 4, the membrane valve 500 includes the position sensor system 212, which comprises two conductive portions: a conductive boss or pad 550 on the membrane 510 and a conductive boss or ring 560 on the valve seat 522. The conductive pad 550 and the conductive ring 560 together form complementary electrical elements of an electrical network or circuit. In the pictured embodiment, when the conductive pad 550 is in contact with the conductive ring 560, the circuit is closed. When the conductive pad 550 is not in contact with the conductive ring 560, the circuit is open. Whether the electrical circuit is closed or open to indicate that the valve 500 is in a closed or open condition, however, is a matter of design logic that may vary between different embodiments. In some embodiments, the conductive ring 560 is coupled to a voltage source (not shown) and a resistor (not shown), whereas in other embodiments, the conductive pad is coupled to a voltage source (not shown) and a resistor (not shown). When the conductive pad 550 is in contact with the conductive ring 560, a voltage drop across the resistor allows an external voltage detector (not shown) to detect the voltage drop. The internal logic of the IOP control system 200 (e.g., in the processor 206) then determines whether the valve 500 is in an open or closed condition based upon the open or closed state of the electrical circuit indicated by position sensor system 212.

Figure 5:
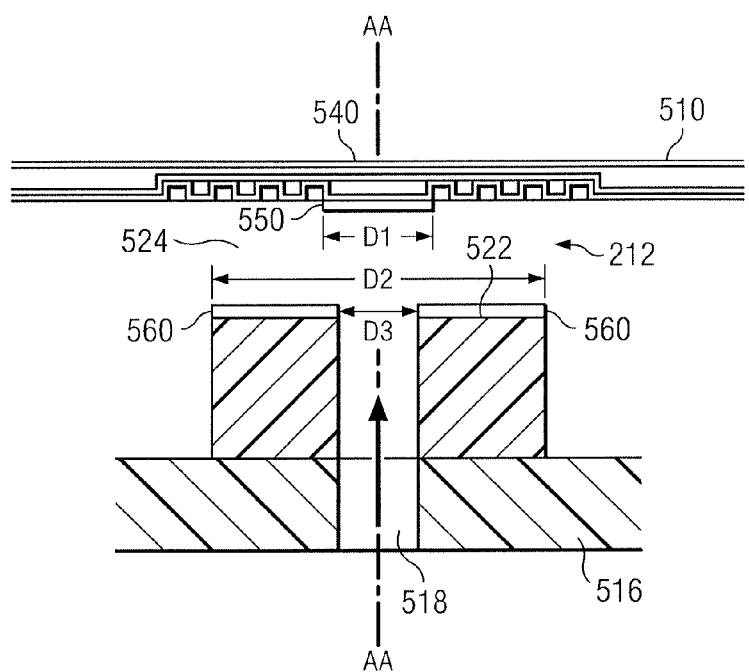
FIG. 5 is an enlarged illustration of a cross-sectional view of the IOP control system shown in FIG. 4, showing an exemplary position sensor system according to one embodiment consistent with the principles of the present disclosure.

The components of the position sensor system 212 are shown in greater detail in FIG. 5. The conductive pad 550 and the conductive ring 560 are aligned with each other about a central axis AA of the housing 516, which extends through the entrance port 518. The conductive pad 550 is positioned on the surface 510b at the central portion 540 of the membrane 510. In the pictured embodiment, the central portion 540 is an uncorrugated portion of the membrane 510. In other embodiments, the central portion may be corrugated. The conductive ring 560 comprises an annular pad that is positioned on the valve seat 522. Thus, both the conductive pad 550 and the conductive ring 560 are adjacent the fluid flow passageway 524 (i.e., in contact with the fluid passing through the valve 500).

Figure 6:
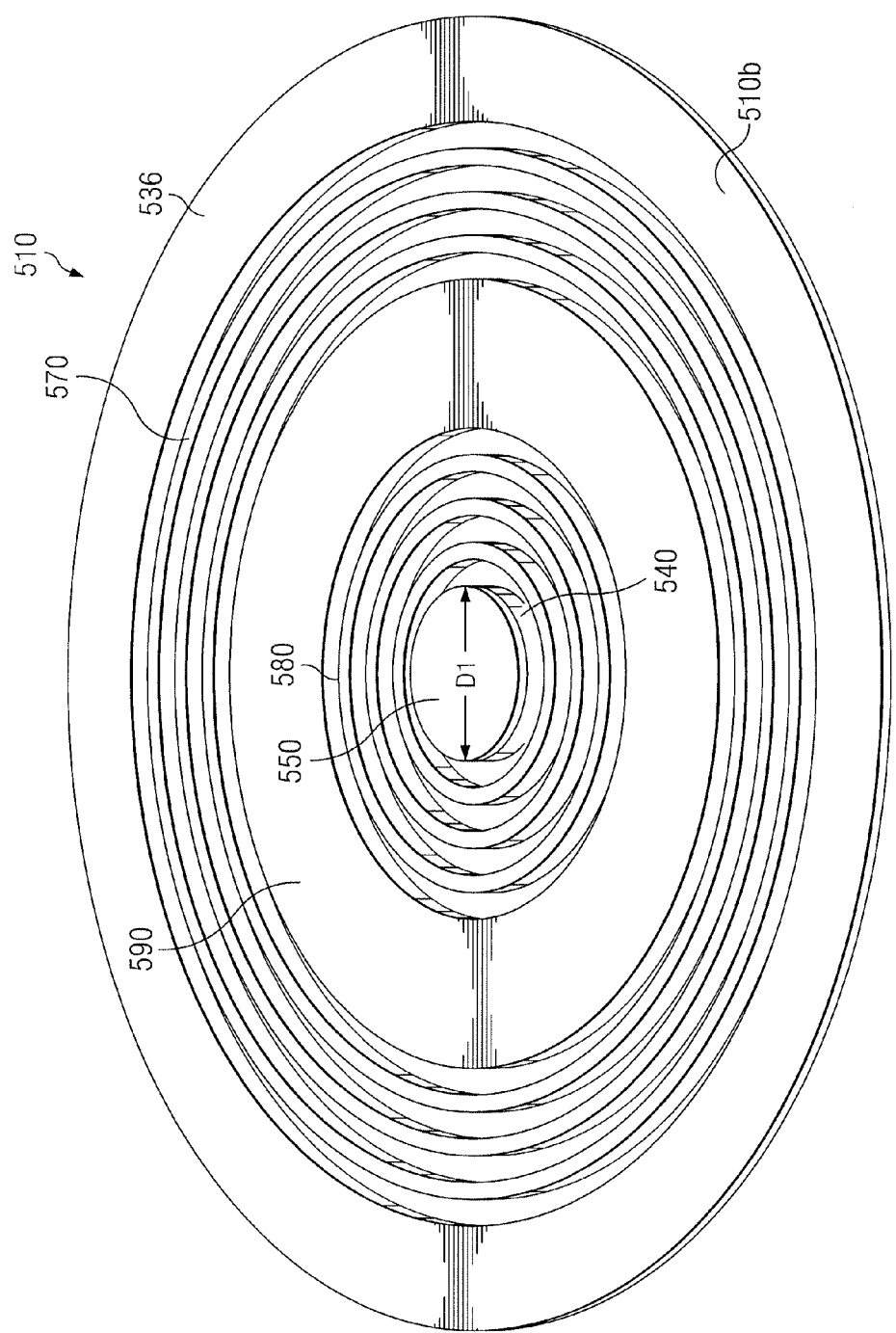
FIG. 6 is a perspective view of an exemplary membrane of the IOP control system shown in FIG. 4, showing an exemplary conductive pad according to one embodiment consistent with the principles of the present disclosure.

In the pictured embodiment shown in FIG. 6, the membrane 510 is shaped and configured as a substantially planar membrane having a circular shape. As mentioned above, the membrane 510 includes concentric corrugation features comprising deep corrugations 570 and shallow corrugations 580 separated by an intermediate zone 590. The shallow corrugations 580 surround the central portion 540. The peripheral zone 536 surrounds the deep corrugations 570. Though the corrugations 570, 580 are shaped and configured as concentric circles, the corrugations are not limited to a particular shape or to a particular combination of shapes.

The conductive pad 550 comprises a circular pad or disc positioned on the surface 510b at the central portion 540 of the membrane 510. The conductive pad 550 is fixedly attached to the membrane 510 by any of a variety of means, including, by way of non-limiting example, vapor deposition, welding, adhesive, and spray fixation. In some embodiments, the conductive pad 550 may be an integral raised part of the membrane 510, such as a raised boss member on the membrane. In other embodiments, the conductive pad 550 may have any of a variety of shapes, including, without limitation, ovoid or polygonal shapes. The conductive pad 550 has an outer diameter D1. The conductive pad 550 may be formed of any of a variety of materials or composite materials having conductive properties, including, but not by way of limitation, gold platinum, titanium, tantalum, doped silicon or any other bio compatible conductive material. Other materials are also contemplated. The conductive pad 550 may have a thickness of less than 0.5 µm, although larger thicknesses are contemplated. In some embodiments, the conductive pad may comprise a conductive film having a nominal thickness. In the pictured embodiment, the conductive pad 550 comprises a disc having a continuous, regular surface of conductive material. In other embodiments, the conductive pad may comprise any of a variety of patterns of conductive material, including, by way of non-limiting example, a grid pattern, a series of protrusions, and a checkerboard pattern. The pattern may be symmetrical or asymmetrical.

Figure 7:
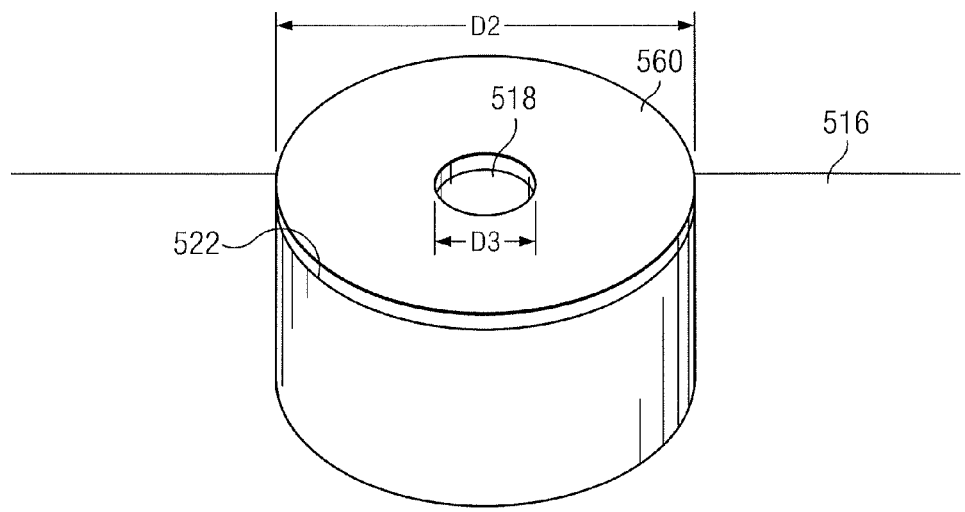
FIG. 7 is a perspective view of an exemplary valve seat of the IOP control system shown in FIG. 4, showing an exemplary conductive ring according to one embodiment consistent with the principles of the present disclosure.

The conductive pad 550 is shaped and configured to contact and form a transient seal against the conductive boss 560 when the membrane 510 is operative within the valve 500. With reference to FIG. 7, the conductive ring 560 comprises an annular or toroid pad or boss positioned on the annular valve seat 522. The conductive ring 560 is fixedly attached to the valve seat 522 by any of a variety of means, including, by way of non-limiting example, vapor deposition, welding, adhesive, and spray fixation. In some embodiments, the conductive ring 560 may be an integral raised part of the valve seat 522, such as a raised boss member on the valve seat. In the pictured embodiment, the conductive ring 560 is shaped to mimic the circular ring shape of the valve seat 522. In other embodiments, the conductive ring may have any of a variety of shapes, including, without limitation, ovoid or polygonal shapes, provided that the conductive ring does not obstruct the entrance port 518. The conductive ring 560 has an outer diameter D2 and an inner diameter D3 (i.e., substantially equivalent to the diameter of the entrance port 518). The conductive ring 560 may be formed of any of a variety of materials or composite materials having conductive properties, including, but not by way of limitation, gold, platinum, titanium, tantalum, doped silicon or any other bio compatible conductive material. Other materials are also contemplated. In some embodiments, the conductive ring 560 is constructed from the same material or composite material as the conductive pad 550. The conductive ring 560 may have a thickness of less than 0.5 µm, although larger thicknesses are contemplated. In some embodiments, the conductive ring may comprise a conductive film having a nominal thickness. In the pictured embodiment, the conductive ring 560 comprises an annular ring having a continuous, regular surface of conductive material. In other embodiments, the conductive ring may comprise any of a variety of patterns of conductive material, including, by way of non-limiting example, a grid pattern, a series of protrusions, and a checkerboard pattern. The pattern may be symmetrical or asymmetrical.

With reference back to FIG. 5, the outer diameter D1 of the conductive pad 550 is less than the outer diameter D2 of the conductive ring 560. In other embodiments, the diameter D1 may be substantially equivalent to or greater than the outer diameter D2 of the conductive ring 560. In the pictured embodiment, the outer diameter D2 of the conductive ring 560 is generally equivalent to the diameter of the valve seat 522. In other embodiments, the outer diameter D2 of the conductive ring 560 may be smaller or larger than the diameter of the valve seat 522. The diameter D1 of the conductive pad 550 is greater than the inner diameter D3 of the conductive ring 560, thereby allowing the conductive pad 550 to contact (i.e., electrically contact) at least a portion of the conductive ring 560 when the membrane 510 deflects towards the valve seat 522 and the valve 500 is in a closed condition. In some embodiments, the diameter D1 may be slightly less than the diameter D3 of the entrance port 518 (i.e., the central opening of the conductive ring 560) such that the conductive pad 550 seats snugly within the central aperture of the conductive ring 560 (and electrically make contact with the each other) when the membrane 510 deflects toward the valve seat 522 and the valve 500 is in a closed condition.

With reference to FIGS. 4 and 5, the fluid flow channel 524 comprises the circumferential gap that arises between the membrane 510 and the conductive ring 560 when the membrane 510 deflects away from the valve seat 522 (i.e., when the conductive pad 550 moves away from the conductive ring 560). The fluid flow channel 524 is a potential space or gap when the membrane 510 rests on the conductive ring 560 such that the conductive pad 550 and the conductive ring 560 are in contact and the valve 500 is in a closed condition. As shown in FIGS. 4 and 5, however, the fluid flow channel 524 enlarges when the membrane 510 deflects off the conductive ring 560 (i.e., away from the valve seat 522) into the flow control chamber 530 and the valve 500 is in an open condition. When the valve 500 is in an open condition, the fluid flow channel 524 is generally an approximate constant width around the annular sealing surface created by the conductive ring 560 (i.e., the gap between the conductive ring 560 and the membrane 510 is generally uniform for a given pressure differential) at any given time.

In use, the IOP control system 200 is implanted in an eye in a conventional manner. The pressure sensors are disposed about the control system 200 in the manner described above. Particularly, the sensor P1 is disposed and configured to measure pressure in the interior eye, sensor P2 is disposed and configured to measure pressure within the valve system, sensor P3 is disposed and configured to measure atmospheric pressure or a reference atmospheric pressure, and sensor P4 is disposed and configured to measure drainage site or bleb pressure.

The IOP control system is configured to adjust the flow through the valve system 230 based on measured pressure values or derivatives from the pressure sensors. If the pressures are not within desired ranges, the IOP control system 200 may adjust the valve system 230 to increase or decrease drainage flow through the drainage tube 330 to effect a pressure change to the desired pressure. To do this, the processor 215 operates the valve system 230 with the power source 205 to activate or deactivate the electrodes 534 in the membrane valve 500 and/or the other structures 512. The electrodes 534 act within the actuator fluid to change at least a portion of the fluid to a gaseous state, increasing the pressure and likewise the volume within the flow control chamber 530. Over time these molecules recombine to change into a fluid state, decreasing the pressure and likewise the volume within the flow control chamber 530. The pressure and the volume changes within the flow control chamber 530 affect the position of the membrane 510 relative to the valve seat 522, thereby influencing whether the valve 500 is in an open or closed condition.

In operation, as the electrodes 534 generate bubbles in the actuator fluid 532 through electrolysis, the pressure increases within the chamber of the flow control chamber 530. As the liquid state partially changes to a gas state, the increasing pressure in the flow control chamber 530 acts against the flexible membrane 510 to displace it and increase the overall volume of the chamber. Thus, as the pressure increases, the membrane 510 expands into the fluid flow passageway 524, decreasing the cross-sectional area of the fluid flow passageway 524, and thereby restricting some fluid flow from the drainage tube 330. In a similar, but opposite manner, as the solution in the flow control chamber 530 returns to its more liquid state, the volume in the flow control chamber 530 decreases, permitting the membrane 510 to move further out of the fluid flow passageway 524, thereby permitting an increased level of fluid flow from the drainage tube 330 through the passageway 524.

In FIGS. 4 and 5, the valve 500 is shown in an open, flow-permitting condition. When the pressure against the surface 510b sufficiently outweighs the pressure against the surface 510a (i.e., the pressure within the flow control chamber 530), the membrane 510 deflects away from the valve seat 522. The circuit created by the position sensor system 212 indicates the flow condition, such as a valve state, to the flow control system 200. When the membrane 510 is deflected away from the valve seat 522, the valve 500 is in an open condition, and the conductive pad 550 does not contact the conductive ring 560. When the conductive pad 550 is not in contact with the conductive ring 560, the circuit created by the position sensor system 212 is open. The open circuit, which indicates the open condition of the valve 500, is communicated to the flow control system 200 and, in particular, the processor 206.

The processor 206 can then make a logic choice based on the data it receives from both the IOP sensor system 210 and the position sensor system 212 (i.e., whether the valve 500 is in an open or closed condition). In particular, if the IOP sensor system 210 indicates that a desirable IOP has been attained, and the position sensor system 212 indicates that the circuit is open, the processor 206 may make a logic choice based on that data to increase the electrolysis within the flow control chamber 530 and deflect the membrane 510 to close the valve 500. The conductive pad 550 on the surface 510b of the membrane 510 is configured to selectively seal against conductive ring 560 overlying the valve seat 522 and thereby close the valve 500 when the pressure against the surface 510a sufficiently outweighs the pressure against the surface 510b. As explained above, the membrane 510 deflects at least partly in response to pressure differences between the fluid flow passageway 524 and the flow control chamber 530 to open and close the valve 500 by changing the dimensions of the fluid flow channel 524. Thus, if the measured IOP is at a desired level, but the open circuit indicates that the valve 500 is open, the processor 206 can cause the valve to assume a closed condition by applying more power to the electrodes 534 within the flow control chamber 530.

It may be desirable not to allow the IOP to drop below a certain threshold or desired level, for example only, 6 mmHg. Intraocular pressure thresholds may be established based on pressure levels considered dangerous to the eye, such as hypotonous pressure levels. If the IOP sensor system 210 indicates that the IOP is below a desirable level, but the open circuit indicates that the valve 500 is still open, the processor 206 can control the valve to assume a closed condition by applying more power to the electrodes 534 within the flow control chamber 530, thereby preventing further decline in IOP and worsening of hypotony.

Figure 8:
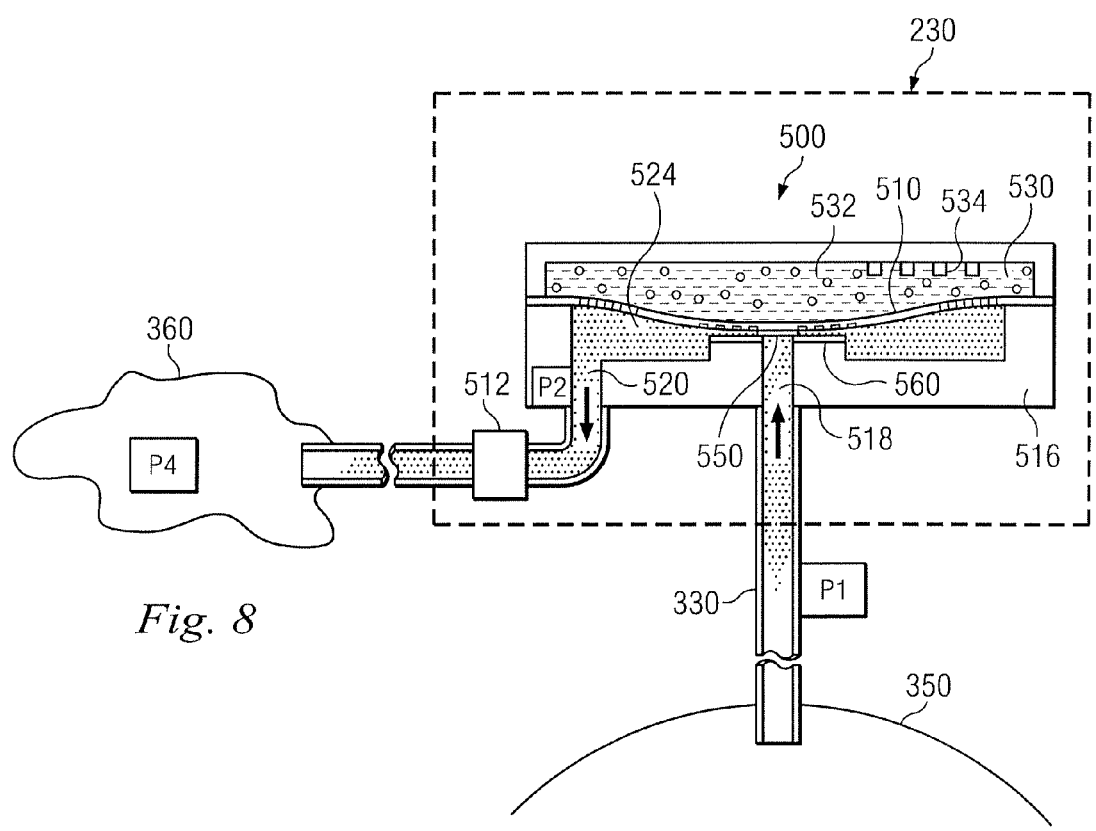
FIG. 8 is an illustration of the exemplary IOP control system shown in FIG. 4 in a closed condition.

In FIG. 8, the valve 500 is shown in a closed, flow-blocking condition. When the pressure against the surface 510a (i.e., the pressure within the flow control chamber 530) sufficiently outweighs the pressure against the surface 510b, the membrane 510 deflects away from the flow chamber 530 toward the entrance port 518. When the membrane 510 is deflected against the conductive ring 560 on the valve seat 522, the valve 500 is in a closed condition, and the conductive pad 550 contacts the conductive ring 560. When the conductive pad 550 contacts the conductive ring, the circuit created by the position sensor system 212 is closed. The closed circuit, which indicates the closed flow condition of the valve 500, is communicated to the flow control system 200 and, in particular, the processor 215. The processor 215 can make a logic choice based on the data it receives from both the IOP sensor system 210 and the position sensor system 212. If the TOP sensor system 210 indicates that a desirable IOP has yet to be attained, or that the IOP is undesirably elevated, and the position sensor system 212 indicates that the circuit is closed, the processor 215 make a logic choice to decrease the electrolysis within the flow control chamber 530, thereby causing the membrane 510 to deflect away from the entrance port 518 to open the valve 500. In order to maintain a desired membrane deflection behavior, these valves often require a continuous supply of energy to generate sufficient gas through electrolysis. If the measured IOP exceeds a desired level, but the closed circuit indicates that the valve 500 is in a closed condition, the processor 215 can cause the valve to assume an open condition by decreasing or eliminating the power supplied to the electrodes 534 within the flow control chamber 530.

It is worth noting that the closed circuit formed by the contact of conductive pad 550 and conductive ring 560 may have several embodiments. The following are several embodiments which are non-limiting and are listed as a means to note examples of implementation. One embodiment utilize the conductive pad 550 and conductive ring 560 as a means of two physical points coming together to close a circuit. Other embodiments consist of a conductive pad split in half where each half is electrically isolated from the other, and a conductive ring is used to bridge the connection. Other embodiments consist of a conductive ring split in half where each half is electrically isolated from the other, and a conductive pad is used to bridge the connection.

It is worth noting that for biocompatibility, the devices disclosed herein may be coated or encapsulated in a material such as polypropylene, silicon, parylene, or other materials.

In a flow control system without a position sensor system, a user would need to measure the flow across the valve to determine if an electrolysis-based valve was in an open or closed condition. This form of detection is rather costly and complex, unlike the form of detection provided by the position sensor system 212 disclosed herein, which requires only the detection of an open or closed electrical circuit and utilizes minimal electronics to determine whether the valve is in an open or closed condition. In addition, because the system is able to recognize whether the valve is open or closed, the position sensor systems disclosed herein allow the flow control system to use power only when necessary, such as to maintain the valve in a closed position only at discrete intervals rather than at all times, thereby optimizing efficient power usage of the device. By aiding the processor to apply energy to the electrodes only when necessary, the position sensor systems disclosed herein reduce the overall amount of energy required and the need for constant energy to power the electrolysis-based valves. Moreover, the cooperative interaction between the IOP sensor system, the position sensor system, and the processor provides a safety feature to electrolysis valves by ensuring that the membrane 510 is not over-pressurized in a situation where the TOP has already attained a desirable level. Over-pressurization of the membrane 510 could lead to structural damage of the membrane.

The devices, systems, and methods described herein achieve IOP control with very low power and with a very small device. The electrolysis-based system accomplishes this using electrolysis and a flexible membrane to affect drainage flow. The exemplary system herein also takes into account intraocular pressures, bleb pressures, and the open or closed condition of the valve in regulating drainage flow.

It is important to note that the devices, systems, and methods described herein can also be utilized to determine the open or closed condition of a pressure-driven membrane valve that is coupled to electronics (e.g., a processor). An electrolysis-based membrane valve responds similarly to a pressure differential membrane valve, except that the electrolysis process is used to control the pressure on one side of the membrane. An exemplary pressure differential membrane valve includes a membrane anchored within a housing to form a reference chamber on a first side of the membrane (i.e., where the flow control chamber is in an electrolysis-based valve) and a fluid flow passsageway on a second opposing side of the membrane. The reference chamber has a reference chamber pressure representative of atmospheric pressure, and the membrane is configured to affect flow through the fluid flow channel in much the same way as the membrane in an electrolysis-based valve, by deflecting in response to pressure differentials between the reference chamber pressure and the fluid flow channel pressure acting on the opposing sides of the membrane. The position sensor systems disclosed herein can assist a processor associated with the pressure-driven membrane valve with logic decision by supplying data relating to the open or closed condition of the valve.

For example, in one embodiment, if the position sensor system informs the processor that the valve is in a closed condition, and the IOP sensor system informs the processor that the TOP is at a desirable level, the processor can make a logic choice to reduce the power to a pump system associated with the pressure-driven membrane valve, thereby increasing the longevity and reliability of valve actuation by minimizing power consumption and extending battery life. However, the position sensor systems will not guard against over-pressurization of the membrane in a pressure differential membrane valve because over-pressurization from ambient pressure is not controllable (and is unlikely).

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An IOP control device for implantation in an eye of a patient, comprising:
    a housing sized for implantation into the eye of the patient and including an entrance port and an exit port;
    a membrane anchored within the housing in a manner forming a flow control chamber on a first side of the membrane and a fluid flow passageway on a second opposing side of the membrane, the flow control chamber including a flow control chamber pressure and the fluid flow passageway including a fluid flow passageway pressure, the membrane configured to affect flow through the fluid flow passageway from the entrance port to the exit port by deflecting in response to pressure differentials of the flow control chamber pressure and the fluid flow channel pressure acting on the opposing sides of the membrane; and
    a position sensor system configured to detect the position of the membrane including:
        a first conductive portion positioned on the membrane; and
        a second conductive portion positioned on the housing between the entrance port and the exit port, and positioned to selectively contact the first conductive portion to indicate the position of the membrane relative to the fluid flow passageway;
        wherein the first and second conductive portions are sized and shaped to form a seal that occludes flow through the fluid flow passageway when the first and second conductive portions are in contact.

2. The IOP control device of claim 1, wherein the first conductive portion is a conductive pad.

3. The IOP control device of claim 2, wherein the second conductive portion is a conductive ring.

4. The IOP control device of claim 2, wherein the conductive pad is positioned on a central portion of the membrane.

5. The IOP control device of claim 2, wherein the conductive pad comprises an integral, raised, central boss portion of the membrane.

6. The IOP control device of claim 2, wherein the conductive pad is fixedly attached to the membrane.

7. The IOP control device of claim 1, wherein the first conductive portion forms a continuous surface of conductive material.

8. The IOP control device of claim 1, wherein the first conductive portion forms a discontinuous surface of conductive material comprising at least a first conductive section and a second conductive section.

9. The IOP control device of claim 1, wherein the first conductive portion includes gold.

10. The IOP control device of claim 1, wherein the second conductive portion forms a continuous annular surface of conductive material.

11. The IOP control device of claim 1, wherein the second conductive portion forms a discontinuous surface of conductive material comprising at least a first conductive section and a second conductive section.

12. The IOP control device of claim 1, wherein the second conductive portion includes gold.

13. The IOP control device of claim 1, wherein the first conductive portion and the second conductive portion are aligned with each other about a central axis of the housing.

14. The IOP control device of claim 1, wherein the position sensor system forms a closed electrical circuit when the first conductive portion contacts the second conductive portion.

15. The IOP control device of claim 8, wherein the position sensor system forms an closed electrical circuit when the second conductive portion contacts and bridges the first conductive section and second conductive section of the first conductive portion.

16. The IOP control device of claim 11, wherein the position sensor system forms an closed electrical circuit when the first conductive portion contacts and bridges the first conductive section and second conductive section of the second conductive portion.

17. The IOP control device of claim 3, wherein the housing further comprises a valve seat circumferentially surrounding the entrance port, and the conductive ring is positioned on the valve seat.

18. The IOP control device of claim 17, wherein the conductive ring comprises an integral, raised, boss portion of the valve seat.

19. The IOP control device of claim 17, wherein the conductive ring is fixedly attached to the valve seat.

20. The IOP control device of claim 3, wherein the conductive pad includes an outer diameter and the conductive ring includes an inner diameter, wherein the outer diameter is greater than the inner diameter.

21. The IOP control device of claim 1, wherein the membrane is shaped and configured as a flexible, corrugated membrane.

22. The IOP control device of claim 1, wherein the flow control chamber is configured to contain a gas creating a flow control chamber pressure, and the flow control chamber includes an actuator fluid and an electrolysis system configured to affect the flow control chamber pressure by generating bubbles by converting at least a portion of the actuator fluid to the gas.

23. The TOP control device of claim 1, wherein the flow control chamber is shaped and configured as a reference pressure chamber having a reference chamber pressure representative of atmospheric pressure.

24. An IOP control system for implantation in an eye of a patient, comprising:
   a drainage tube configured to convey aqueous humor from an anterior chamber of the eye; and
   a flow system in fluid communication with the drainage tube and including:
      a housing including a valve seat positioned between an entrance port and an exit port from the drainage tube;
      a membrane, the membrane anchored within the housing to form a flow control chamber having a flow control chamber pressure on a first side of the membrane, the implantable device being actuatable in response to a flow control chamber pressure and the membrane being configured to control flow rates of the aqueous humor along the drainage tube by deflecting in response to the flow control chamber pressure; and
      a position sensor system including:
         a first conductive portion positioned on the membrane; and
         a second conductive portion positioned on the valve seat between the entrance port and the exit port;
      wherein the first and second conductive portions are sized and shaped to form a seal that occludes flow of the aqueous humor through the drainage tube when the first and second conductive portions are in contact.

25. The IOP control system of claim 24, wherein the first conductive portion and the second conductive portion are aligned with each other about a central axis extending through the valve seat.

26. The IOP control system of claim 24, wherein the first conductive portion is fixedly attached to a central portion of the membrane.

27. The IOP control system of claim 24, wherein the first conductive portion comprises an integral, raised, central boss portion of the membrane.

28. The IOP control system of claim 24, wherein the second conductive portion comprises an integral, raised, boss portion of the valve seat.

29. The IOP control system of claim 28, wherein the second conductive portion is fixedly attached to the valve seat.

30. The IOP control system of claim 24, wherein the first conductive portion comprises a disc including an outer diameter and the second conductive portion comprises a ring including an inner diameter, wherein the outer diameter is greater than the inner diameter.

31. The IOP control system of claim 24, wherein the position sensor system forms a closed electrical circuit when the first conductive portion contacts the second conductive portion.

32. The IOP control system of claim 24, wherein the position sensor system forms an open electrical circuit when the first conductive portion contacts the second conductive portion.

33. A method of regulating drainage from an anterior chamber of an eye with an implantable device, comprising:
   directing fluid from an entrance port through a fluid flow passageway formed in part by a flexible membrane, the membrane configured to deflect away from and toward a valve seat to throttle flow by increasing or decreasing the size of the fluid flow passageway;
   determining a valve state of the implantable device using a position sensor system configured to detect a position of the membrane relative to the valve seat, wherein determining a valve state comprises detecting a voltage change with a position sensor system, the position sensor system comprising a first conductive portion on the membrane in alignment with a second conductive portion on the valve seat; and
   modifying the amount of drainage through the implantable device in response to a flow control pressure acting on the membrane by deflecting the membrane to increase or decrease the size of the fluid flow passageway based on the valve state of the implantable device, wherein deflecting the membrane comprises contacting the first and second conductive portions of the position sensor system to form a seal that occludes flow of the fluid through the fluid flow passageway.

34. The method of claim 33, wherein an electrolysis process using electrodes affects the flow control pressure acting on the membrane.

35. The method of claim 34, wherein modifying the amount of drainage through the implantable device comprises increasing or decreasing power to the electrodes.

36. The method of claim 35, wherein increasing or decreasing power to the electrodes comprises decreasing power to the electrodes when the position sensor system detects that the fluid flow passageway is closed.

37. The method of claim 33, wherein determining a valve state of the implantable device comprises determining whether the valve state of the implantable device is open with fluid flowing from the entrance port into the fluid flow passageway or closed with fluid not flowing from the entrance port into the fluid flow passageway.

38. The method of claim 33, wherein modifying the amount of drainage through the implantable device comprises controlling deflection of the membrane to increase or decrease the size of the fluid flow passageway in response to a closed looped pressure control signal.

39. The IOP control device of claim 1, wherein the membrane further comprises first corrugation features proximate to the first conductive portion and second corrugation features spaced from the first corrugation features, wherein depths of the first and second corrugations features are different.

* * * * *